(12) United States Patent
Shapiro (10) Patent No.: US 8,071,551 B2
(45) Date of Patent: Dec. 6, 2011

(54) METHODS AND COMPOSITIONS FOR TREATING DIABETES

(75) Inventor: Leland Shapiro, Denver, CO (US)

(73) Assignee: BioHolding, Inc., Wilson, NC (US)

( * ) Notice: Subject to any disclaimer, the term of this patent is extended or adjusted under 35 U.S.C. 154(b) by 803 days.

(21) Appl. No.: 12/051,373

(22) Filed: Mar. 19, 2008

(65) Prior Publication Data
US 2008/0261868 A1  Oct. 23, 2008

Related U.S. Application Data

(63) Continuation of application No. 09/518,081, filed on Mar. 3, 2000, now Pat. No. 7,704,958.

(60) Provisional application No. 60/123,167, filed on Mar. 5, 1999, provisional application No. 60/123,523, filed on Mar. 8, 1999.

(51) Int. Cl.
*A61K 38/57* (2006.01)
*C12N 15/15* (2006.01)

(52) U.S. Cl. ..................... 514/20.3; 435/69.2

(58) Field of Classification Search .......... None
See application file for complete search history.

(56) References Cited

U.S. PATENT DOCUMENTS

| | | | |
|---|---|---|---|
| 4,629,567 A * | 12/1986 | Bollen et al. ............ 210/635 |
| 4,711,848 A * | 12/1987 | Insley et al. ............ 435/69.2 |
| 4,829,054 A | 5/1989 | Emerson et al. |
| 5,040,545 A * | 8/1991 | Dutcher et al. ......... 607/131 |
| 5,134,119 A | 7/1992 | Lezdey et al. |
| 5,187,089 A | 2/1993 | Scott et al. |
| 5,216,022 A | 6/1993 | Oleksyszyn et al. |
| 5,314,910 A | 5/1994 | Kirschenheuter et al. |
| 5,346,886 A | 9/1994 | Lezdey et al. |
| 5,376,655 A | 12/1994 | Imaki et al. |
| 5,399,346 A | 3/1995 | Anderson et al. |
| 5,416,191 A | 5/1995 | Cheronis et al. |
| 5,420,110 A | 5/1995 | Miller et al. |
| 5,432,178 A | 7/1995 | Nakai et al. |
| 5,470,970 A | 11/1995 | Saeger et al. |
| 5,476,995 A | 12/1995 | Clark et al. |
| 5,478,727 A | 12/1995 | Roizman et al. |
| 5,486,470 A | 1/1996 | Darke et al. |
| 5,492,889 A | 2/1996 | Lezdey et al. |
| 5,514,653 A | 5/1996 | Perlmutter |
| 5,514,713 A | 5/1996 | Nakai et al. |
| 5,529,920 A | 6/1996 | Cole et al. |
| 5,532,215 A | 7/1996 | Lezdey et al. |
| 5,565,334 A | 10/1996 | Kufe et al. |
| 5,593,858 A | 1/1997 | Fleer et al. |
| 5,604,201 A | 2/1997 | Thomas et al. |
| 5,610,140 A | 3/1997 | Goodfellow et al. |
| 5,610,285 A | 3/1997 | Lebing et al. |
| 5,614,555 A | 3/1997 | Nakai et al. |
| 5,616,693 A | 4/1997 | Hwang et al. |
| 5,618,792 A | 4/1997 | Gyorkos et al. |
| 5,622,984 A | 4/1997 | Nakai et al. |
| 5,635,593 A | 6/1997 | Cheronis et al. |
| 5,641,670 A | 6/1997 | Treco et al. |
| 5,663,416 A | 9/1997 | Kirschenheuter et al. |
| 5,665,589 A | 9/1997 | Harris et al. |
| 5,700,779 A | 12/1997 | Goodfellow et al. |
| 5,710,026 A | 1/1998 | Sprecher |
| 5,712,117 A | 1/1998 | Sprecher |
| 5,747,645 A | 5/1998 | Sprecher |
| 5,750,506 A | 5/1998 | Goodfellow et al. |
| 5,759,548 A | 6/1998 | Bathurst et al. |
| 5,780,009 A | 7/1998 | Karatzas et al. |
| 5,780,440 A | 7/1998 | Lezdey et al. |
| 5,798,442 A | 8/1998 | Gallant et al. |
| 5,801,148 A | 9/1998 | Gyorkos et al. |
| 5,807,829 A | 9/1998 | Gyorkos et al. |
| 5,811,241 A | 9/1998 | Goodfellow et al. |
| 5,817,484 A | 10/1998 | Yu et al. |
| 5,834,431 A | 11/1998 | Stewart et al. |
| 5,843,900 A | 12/1998 | Cheronis et al. |
| 5,849,863 A | 12/1998 | Stewart et al. |
| 5,861,299 A | 1/1999 | Archibald et al. |
| 5,861,380 A | 1/1999 | Gyorkos et al. |
| 5,863,899 A | 1/1999 | Cheronis et al. |

(Continued)

FOREIGN PATENT DOCUMENTS

WO   93/18794 A1   9/1993

(Continued)

OTHER PUBLICATIONS

Ihse, I., et al., 1976, "Oral trypsin-inhibitor-induced improvement of the exocrine and endocrine pancreatic functions in alloxan diabetic rats", Scandinavian Journal of Gastroenterology, vol. 11, pp. 363-368.*

(Continued)

*Primary Examiner* — Manjunath Rao
*Assistant Examiner* — William W Moore
(74) *Attorney, Agent, or Firm* — Faegre & Benson LLP (57) ABSTRACT

The instant invention provides a method of treating an animal suffering a disease characterized by excessive apoptosis by administering a therapeutically effective amount of at least one serine protease inhibitor and thereafter monitoring a decrease in apoptosis. The inhibitor of the invention includes $\alpha_1$-antitrypsin or an $\alpha_1$-antitrypsin-like agent, including, but not limited to oxidation-resistant variants of $\alpha_1$-antitrypsin, and peptoids with antitrypsin activity. The diseases treatable by the invention include cancer, autoimmune disease, sepsis neurodegenerative disease, myocardial infarction, stroke, ischemia-reperfusion injury, toxin induced liver injury and AIDS. The method of the invention is also suitable for the prevention or amelioration of diseases characterized by excessive apoptosis.

7 Claims, 2 Drawing Sheets

U.S. PATENT DOCUMENTS

| | | | |
|---|---|---|---|
| 5,869,455 | A | 2/1999 | Gyorkos et al. |
| 5,874,424 | A | 2/1999 | Batchelor et al. |
| 5,874,585 | A | 2/1999 | Gyorkos et al. |
| 5,891,852 | A | 4/1999 | Gyorkos et al. |
| 6,022,969 | A | 2/2000 | Rice et al. |
| 6,110,949 | A * | 8/2000 | Villhauer ............... 514/365 |
| 6,124,257 | A | 9/2000 | Lezdey et al. |
| 6,313,117 | B1 * | 11/2001 | Bekkali et al. .......... 514/235.5 |
| 6,566,331 | B1 | 5/2003 | Lezdey et al. |
| 2002/0049164 | A1 * | 4/2002 | Demuth et al. ............ 514/19 |
| 2002/0058809 | A1 * | 5/2002 | Emmanuel et al. .......... 544/60 |
| 2004/0220239 | A1 | 11/2004 | Shapiro |
| 2004/0220242 | A1 | 11/2004 | Shapiro |

FOREIGN PATENT DOCUMENTS

| | | | |
|---|---|---|---|
| WO | 94/07525 | A1 | 4/1994 |
| WO | 95/28422 | A1 | 10/1995 |
| WO | 95/34538 | A2 | 12/1995 |
| WO | 96/12021 | A2 | 4/1996 |
| WO | 96/14067 | A1 | 5/1996 |
| WO | 97/03679 | A1 | 2/1997 |
| WO | 97/09346 | A1 | 3/1997 |
| WO | 97/09347 | A1 | 3/1997 |
| WO | 97/10222 | A1 | 3/1997 |
| WO | 97/10231 | A1 | 3/1997 |
| WO | 97/21690 | A1 | 6/1997 |
| WO | 97/24339 | A1 | 7/1997 |
| WO | 97/31937 | A1 | 9/1997 |
| WO | 97/33996 | A2 | 9/1997 |
| WO | 97/37969 | A1 | 10/1997 |
| WO | 97/45402 | A1 | 12/1997 |
| WO | 97/48706 | A1 | 12/1997 |
| WO | 97/49679 | A1 | 12/1997 |
| WO | 98/06417 | A1 | 2/1998 |
| WO | 98/09206 | A1 | 3/1998 |
| WO | 98/20034 | A2 | 5/1998 |
| WO | 98/21186 | A1 | 5/1998 |
| WO | 98/22098 | A2 | 5/1998 |
| WO | 98/22619 | A1 | 5/1998 |
| WO | 98/23565 | A2 | 6/1998 |
| WO | 98/24806 | A2 | 6/1998 |
| WO | 98/46597 | A1 | 10/1998 |
| WO | 98/49190 | A2 | 11/1998 |
| WO | 98/50342 | A1 | 11/1998 |
| WO | 98/50420 | A1 | 11/1998 |
| WO | 98/56821 | A1 | 12/1998 |
| WO | 99/41231 | A1 | 8/1999 |
| WO | 99/43308 | A2 | 9/1999 |
| WO | 00/44390 | | 8/2000 |
| WO | 00/52034 | | 9/2000 |

OTHER PUBLICATIONS

Nakamura, N., et al. 1980, "Effect of trypsin inhibitor on blood sugar, insulin, and glucagon levels in normal and streptozotocin rats", Journal of the Kyoto Prefecture University of Medicine, vol. 89, No. 6, pp. 465-470.*

Katsura, M., et al., 1992, "Effect of long-term oral administration of trypsin inhibitor on pancreatic exocrine dysfunction in non-insulin dependent diabetes mellitus (NIDDM)", Journal of Pancreas, vol. 7, No. 2, pp. 1-8.*

Katsura, M., et al., 1992, Journal of Pancreas, English Translation, 23 pages.*

Shimoda, I., et al., 1993, "Physiological characteristics of spontaneously developed diabetes in male WBN/Kob rat and prevention of development of diabetes by chronic oral administration of synthetic trypsin inhibitor (FOY-305)", Pancreas, vol. 8, No. 2, pp. 196-203.*

Ikeda, T., et al., 1996, "An inhibition of urinary albumin excretion by protease inhibitor in streptozotocin-diabetic rats", Nephron, vol. 74, No. 4, pp. 709-712.*

Kurtz, T.W., et al., 1988, "Transcription-modulating drugs: A new frontier in the treatment of essential hypertension", Hypertension, vol. 32, No. 3, pp. 380-386.*

Ebeling, P., et al., 1999, "Troglitazone reduces hyperglycaemia and selectively acute-phase serum proteins in patients with Type II diabetes", Diabetologia, vol. 42, No. 12, pp. 1433-1438.*

Davis, S.N., et al., 1999, "Insulin use in the elderly", Journal of Geriatric Drug Therapy, vol. 12, No. 2, pp. 61-81.*

Adelman S.F. et al., "Protease inhibitors suppress fibrinolytic activity of herpesvirus-transformed cells", J Gen Virol, 1982, 60(Pt 1):15-24.

Altieri, D.C. J Leukoc Biol 1995, 58, pp. 120-127.

Ancliff, P.J., et al., 2001, "Mutations in the ELA2 gene encoding neutrophil elastase are present in most patients with sporadic severe congenital neutropenia but only in some patients with the familial form of the disease", Blood, vol. 98, pp. 2645-2650.

Anderson Ed, Thomas L, Hayflick Js, Thomas G., "Inhibition of HIV-1 gp160-dependent membrane fusion by a furin-directed alpha 1-antitrypsin variant", J Biol Chem, 268(33):24887-91 (Nov. 25, 1993).

Aoki H, Akaike T, Abe K, Kuroda M, Arai S, Okamura R, Negi A, Maeda H. Antiviral effect of oryzacystatin, a proteinase inhibitor in rice, against herpes simplex virus type I in vitro and in vivo. Antimicrob Agents Chemother Apr. 1995;39(4):846-9.

Aprikyan, A.A.G., et al., 2001, "Mutations in the neutrophil elastase gene in cyclic and congenital neutropenia", Current Opinion in Immunology, vol. 13, pp. 535-538.

Auerswald et al., "K15R M52E) aprotinin is a weak Kunitz-type inhibitor of HIV-1 replication in H9 cells" Biomed Biochim Acta, 1991, 50(4-6):697-700.

Auerswald et al., "Recombinant leech-derived tryptase inhibitor: construction, production, protein chemical characterization and inhibition of HIV-1 replication", Biol Chem Hoppe Seyler, 375(10):695-703 (1994).

Avril Le, Di Martino-Ferrer M, Barin F, Gauthier F., "Interaction between a membrane-associated serine proteinase of U-937 monocytes and peptides from the V3 loop of the human immunodeficiency virus type I (HIV-1) gp120 envelope glycoprotein", FEBS Lett, 317(1-2):167-72 (Feb. 8, 1993).

Avril, et al., "Identification of the U-937 membrane-associated proteinase interacting with the V3 loop of HIV-1 gp120 as cathepsin G", FEBS Lett, 1994, 345(1):81-6.

Banfi G, Pirali A, Locatelli M, Murone M, Bonini Pa., "Tumor-associated trypsin inhibitor in induced and acquired immunodeficiency. Studies on transplanted and HIV-infected patients", Scand J Clin Lab Invest, 51 Suppl, 207:55-8 (1991).

Barker, A. F. et al., 1997, "Pharmacokinetic study of alpha1-antitrypsion infusion in alpha1-antitrypsin deficiency", Chest, vol. 112, pp. 607-613.

Beal, M.F., "Mitochondria, Free Radicals, and Neurodegeneration", Curr. Opin. Neurobiol., 1996, 6, 661-666.

Beard, S., et al., 2008, Alpha-1-antitrypsin is an inhibitor of intracellular pro-inflammatory cytokine production in monocytes and T-cells, conference poster exhibit, sheets 1-9.

Beck, K.F. et al. in J Exp Biol 1999, 202, pp. 645-653.

Best, P.J.M. et al., "Apoptosis", Arteriosclerosis, Thrombosis, and Vascular Biology, 1999, 19, 14.-22.

Bjorck L, Grubb A, Kjellen L. Cystatin C, a human proteinase inhibitor, blocks replication of herpes simplex virus. J Virol Feb. 1990;64(2):941-3.

Bogdan, I., et al., 1997, "Tumor necrosis factor-.alpha. contributes to apoptosis in hippocampal neurons during experimental group B *Streptococcal meningitis*", The Journal of Infectious Diseases, vol. 176, pp. 693-697.

Bourinbaiar As, Lee-Huang S., "Acrosin inhibitor, 4'-(acetamidophenyl 4-guanidinobenzoate, an experimental vaginal contraceptive with anti-HIV activity", Contraception, 51(5):319-22 (May 1995).

Bourinbaiar As, Nagorny R., "Effect of serine protease inhibitor, N-alpha-tosyl-L-lysyl-chloromethyl ketone (TLCK), on cell-mediated and cell free HIV-1 spread", Cell Immunol, 155(1):230-6 (Apr. 15, 1994).

Bratt J, Palmblad J. Cytokine-induced neutrophill 5 mediated injury of human endothelial cells. J Immunol Jul. 15, 1997; 159(2):812-8.

Brinkmann T, Schafers J, Gurtler L, Kido H, Niwa Y, Katunuma N, Tschesche H., "Inhibition of tryptase TL2 from human T4+ lymphocytes and inhibition of HIV-1 replication of H9 cells by recombinant aprotinin and bikunin homologues", J Protein Chem, 16(6):651-60) (Aug. 1997).

Bristow CL, Fiscus SA, Flood PM, Arnold RR:, "Inhibition of HIV-1 by modification of a host membrane protease", Int Immunol, 7(2):239-49 (Feb. 1995).

Bukrinskaia AG, Kitsak Vla, Moisiadi SA, Arakelov SA. Suppression of rotavirus SA-II reproduction by protease inhibitors in cell culture. Vopr Virusol Jan.-Feb. 1987;32(1):71-4, English abstract only at p. 74.

Bukrinskaia AG, Korneeva MN, Nosik DN, Zhdanov VM., "Inhibition of HIV reproduction in cultured cells using proteolysis inhibitors", Vopr Virusol, 34(1):53-5 (Jan.-Feb. 1989), English Abstract only at p. 55.

Carroccio A, Fontana M, Spagnuolo MI, Zuin G, Montalto G, Canani RB, Verghi F, Di Martino D, Bastoni K, Buffardi F, Guarino A., "Pancreatic dysfunction and its association with fat malabsorption in HIV infected children",Gut,43(4):558-63 (Oct. 1998).

Casolaro, M. A., et al., 1987, "Augmentation of lung neutrophil elastase capacity with recombinant human alpha-1-antitrypsin", Journal of Applied Physiology, vol. 63, pp. 2015-2023.

Chesnokova NB, Kasavina BS, Maichuk IuF, Kazachenko MA, Shchipanova Al. Main proteolytic inhibitors in ocular herpes. Vopr Med Khim Sep.-Oct. 1981;27(5):663-5, English Abstract.

Chesnokova NB, Maichuk YF. Antiproteases in herpetic keratitis. Metab Pediatr Syst Ophthalmol 1986;9(1):593-6.

Cilberto et al., 1995, Cell, 41:531-540.

Cordiali Fei et al., "Behavior of several 'progression markers' during the HIV-Ab seroconversion period. Comparison with later stages", J Biol Regul Homeost Agents, 6(2):57-64 (Apr.-Jun. 1992).

Cowan, B., et al., 1996, "Elafin, a serine protease inhibitor, attenuates post-cardiac transplant coronary arteriopathy and reduces myocardial necrosis in rabbits after heterotropic transplantation", Journal of Clinical Investigation, vol. 97, pp. 2452-2468.

Cox et al., "Synergistic combinations and peptides in the inhibition of human immunodeficiency virus", Adv Enzyme Regul, 31:85-97 (1991).

Daemen, M.A.R. C., et al., 2000, "Functional protection by acute phase proteins alpha1-acid glycoprotein and alpha1-antitrypsin against ischemia/reperfusion injury by preventing apoptosis and inflammation", Circulation, vol. 102, pp. 1420-1426.

Deam DR, Byron KA, Ratnaike S, Campbell DG, Mulhall BP, Mackay IR., "Alpha I-antitrypsin phenotypes in homosexual men", Pathology, 21(2):91-2 (Apr. 1989).

Decroly E, Wouters S, Di Bello C, Lazure C, Ruysschaert JM, Seidah NG., "Identification of the paired basic convertases implicated in HIV gp 160 processing based on in vitro assays and expression in CD4(+) cell lines", J Biol Chem, 271(48):30442-50 (Nov. 1996).

Deigner, H.P. et al., "Modulating Apoptosis: Current Applications and Prospects for Future Drug Development", Current Medicinal Chemistry, 1999, 6, 399-414.

Dery, O. and Bunnett, N. W. Biochem Soc Trans 1999, 2 7,246-254.

Dery, O. et al. Am J Physiol 1998, 2 74, C 1429-C 1452.

DiLanni CL, Drier DA, Deckman IC, McCann PJ 3d, Liu F, Roizinan B, Colonno RJ, Cordingley MG. Identification of the herpes simplex virus-I protease cleavage sites by direct sequence analysis of autoproteolytic cleavage products. Biol Chem Jan. 25, 1993;268(3):2048-51.

Dilanni CL, Stevens JT, Bolger M, O'Boyle DR 2nd, Weinheimer SP, Colonno RJ. Identification of the serine residue at the active site of the herpes simplex virus type 1 protease. J Biol Chem Apr. 29, 1994;269(17):12672-6.

Ding, A. et al., in J. Immunol. 1990, 145, 940.

Estaquier J, Tanaka M, Suda T, Nagata S, Golstein P, Ameisen JC. Fas-mediated apoptosis of CD4+ and CD8+ T cells from human immunodeficiency virus-infected persons: differential in vitro preventive effect of cytokines and protease antagonists. Blood Jun. 15, 1996;87(12):4959-66.

Flaitz CM, Hicks MJ. "Molecular piracy: the viral link to carcinogenesis." Oral Oncol Nov. 1998;34(6):448-53.

Franzusoff A, Volpe AM, Josse D, Pichuantes S, Wolf Jr., "Biochemical and genetic definition of the cellular protease required for HIV-1 gp160 processing", J Biol Chem Feb. 17, 1995;270(7):3154-9.

George, P.M., et al., 1984, "A genetically engineered mutant of alpha1-antitrypsin protects connective tissue from neutrophil damage and 05—be useful in lung disease", The Lancet, vol. 2, pp. 1426-1428.

Glozman VN, "Immunologic foundation of enzyme therapy of patients with orchiepididymitis", Antibiot Khimioter, 35(7):50-52 (Jul. 1990), English abstrtact @ p. 52.

Glynn JM, McElligott DL, Mosier DE. Apoptosis induced by HIV 5 infection in H9 T cells is blocked by Ice-family protease inhibition but not by a Fas(CD95) antagonist. J Immunol Oct. 1, 1996;157(7):2754-2758.

Goureau, O. et al., in Proc. Natl. Acad. Sci. U.S.A. 1993, 90, 4276.

Griffin, William C. , "Calculation of HLB Values of Non-Ionic Sufactants", [H. L. B.—The Hydrophilic-Lipophilic Balance], J. Soc. Cos. Met. Chem., vol. 5, p. 249 (1954).

Grodzicky, T., et al., 2000, "Apoptosis in rheumatic diseases", American Journal of Medicine, vol. 108, pp. 73-82.

Gu M, Rappaport J, Leppla SH., "Furin is important but not essential for the proteolytic maturation of gp160 of HIV-1", FEBS Lett, 22;365(1):95-7 (May 10, 1995).

Hallenberger S, Bosch V, Angliker H, Shaw E, Klenk HD, Garten W., "Inhibition of furin-mediated cleavage activation of HIV-1 glycoprotein gp160", Nature, 26;360(6402):358-61(Nov. 26, 1992).

Harvima et al., "Separation and partial characterization of proteinases with substrate specificity for basic amino acids from human MOLT-4 T lymphocytes: identification of those inhibited by variable-loop-V3 peptides of HIV-1 (human immunodeficiency virus-I) envelope glycoprotein", Biochem J, 292 (Pt 3):711-8 (1993).

Heck, D. E. et al., in J. Biol. Chem. 1990, 267, 21277.

Herbert, J.M., et al., 1992, "Biochemical and pharmacological activities of SR 26831, a potent and selective elastase inhibitor", The Journal of Pharmacology and Experimental Therapeutics, vol. 260, No. 2, pp. 809-816.

Hetts, S.W., 1998, "To die or not to die—An overview of apoptosis and its role in disease", Journal of the American Medical Association, vol. 279, No. 4, pp. 300-307.

Holwerda BC. Herpesvirus.proteases: targets for novel antiviral drugs. Antiviral Res Jun. 1997;35(1):1-21.

Honig, L.S., et al., 2000, "Apoptosis and neurologic disease", American Journal of Medicine, vol. 108, pp. 317-330.

Hubbard, R.C. et al., 1988, "Alpha-1-antitrypsin augmentation therapy for alpha-1-antitrypsin deficiency", The American Journal of Medicine, vol. 84 (Suppl. 6a), pp. 52-62.

Inocencio et al., "Endoprotease activities other than furin and PACE4 with a role in processing of HIV-I gp160 glycoproteins in CHO-K I cells", J Biol Chem, 272(2):1344-8 (1997).

Jabs, T., "Reactive Oxygen Intermediates as Mediators of Programmed Cell Death in Plants and Animals", Biochem. Pharmacol., 1999, 57, 231-245.

James, T.N., et al., 2000, "Apoptosis in cardiac disease", American Journal of Medicine, vol. 108, pp. 606-620.

Kamoshita K, Shiota M, Sasaki M, Koga Y, Okumura Y, Kido H., "Calcium requirement and inhibitor spectrum for intracellular HIV type 1 gp160 processing in cultured HeLa cells and CD4+ ymphocytes: similarity to those of viral envelope glycoprotein maturase", J Biochem, Jun.;117(6):1244-53 (Tokyo Jun. 1995).

Kasahara, Y., et al., 2000, "Inhibition of VEGF receptors causes lung cell apoptosis and emphysema", The Journal of Clinical Investigation, vol. 106, No. 11, pp. 1311-1319.

Kaufman, S. et al., "Specific proteolytic Cleavage of Poly(ADP-ribose) Polymerase: An Early Marker of Chemotherapy-Induced Apoptosis", Cancer Res, 1993, 53, 3976-3985.

Kennedy S, Davis C, Abrams WR, Billings PC, Nagashunmugam T, Friedman H, Malamud D., "Submandibular salivary proteases: lack of a role in anti-HIV activity", J Dent Res, 77(7):1515-9 (Jul. 1998).

Kidd, V.J., "Proteolytic Activities that Mediate Apoptosis", Annu. Rev. Physiol., 1998, 60, 533-573.

Kido H, Fukutomi A, Katunuma N., "A novel membrane-bound serine esterase in human T4+ lymphocytes immunologically reactive with antibody inhibiting syncytia induced by HIV-1. Purification and characterization", J Biol Chem., 15:265 (35):21979-85 (Dec. 1990).

Kido H, Niwa Y, Beppu Y, Towatari T. Cellular proteases involved in the pathogenicity of enveloped animal viruses, human immunodeficiency virus, influenza virus A and Sendai virus. Adv Enzyme Regul 1996;36:325-47.

Kirkeboen, K.A. and Strand, O.A. In Acta Anaesthesiol Scand 1999, 43, 275.

Koito A, Hattori T, Murakami T, Matsushita S, Maeda Y, Yamamoto T, Takatsuki K., "A neutralizing epitbpe of human immunodeficiency virus type 1 has homologous amino acid sequences with the active site of interalpha-trypsin inhibitor", Int Immunol, 1(6):613-8 (1989).

Langer, R. Nature 1998, 392, pp. 5-10.

Lima AA, Silva TM, Gifoni AM, Barrett I-J, McAuliffe IT, Bao Y, Fox JW, Fedorko DP, Guerrant RL., "Mucosal injury and disruption of intestinal barrier function in HIV-infected individuals with and without diarrhea and cryptosporidiosis in northeast Brazil", Am J Gastroenterol, 92(10):1861-6 (Oct. 1997).

Lomas DA, Elliott PR, Carrell RW. Commercial plasma alphal-antitrypsin (Prolastin) contains a conformationally inactive, latent component. Eur Respir J Mar. 1997;10(3):672-5.

Lowenstein C. J. et al. in Proc. Natl. Acad. Sci. USA, 1993, 90, 9730-9734.

Lowenstein, C. J. and Snyder, S.H. in Cell 1992, 70, 705-707.

Madidhara, R., et al., 2000, "Apoptosis in sepsis", Critical Care Medicine, vol. 28, pp. N105-N113.

McCall, T.B. et al., in Biochem. Biophys. Res. Commun. 1992,186, 680-685.

McNeely TB, Dealy M, Dripps DJ, Orenstein JM, Eisenberg SP, Wahl SM, "Secretory leukocyte protease inhibitor: a human saliva protein exhibiting anti-human immunodeficiency virus I activity in vitro", J Clin Invest, 96(1):456-64 (Jul. 1995).

Meki AR, Mohey El-Dean ZM. Serum interleukin-Ibeta, interleukin-6, nitric oxide and alphal-antirypsin in scorpion envenomed children. Toxicon Dec. 1998;36(12):1851-9.

Merrifield, R.B., "Solid Phase Peptide Synthesis. 1. The Synthesis of a Tetrapeptide", J. Am. Chem. Soc. vol. 85, pp. 2149-2154 (1963).

Meylan et al., "HIV infectivity is not augmented by treatment with trypsin, Factor Xa or human mast-cell tryptase", AIDS, 6(1):128-30 (1992).

Miranda et al., "Isolation of the human PC6 gene encoding the putative host protease for HIV-I gp160 processing in CD4+ T lymphocytes", Proc Natl Acad Sci USA, 93(15):7695-7700) (1996).

Molle W. et al. in J Immunol 1997, 159, 3555-3564.

Morel, Jean-Benoit et al., "The Hypersensitive Response and the Induction of Cell Death in Plants", Cell Death and Differentiation, 1997, 4, 671-683.

Moulard M, Achstetter T, Kieny MP, Montagnier L, Bahraoui E, "Kex2p: a model for cellular endoprotease processing human immunodeficiency virus type 1 envelope glycoprotein precursor", Eur J Biochem, 225(2):565-72 (Oct. 15, 1994).

Myagkov, I. I., et al., 1989, "Clinical significance of the alpha-1 proteinase inhibitor in myocardial infarction", Vrachebnoye delo, vol. 1, pp. 32-34. Both Russian-language original and English-language translation.

Nathan, C. in FASEB J. 1992, 6, 3051-3064.

Nierhoerster, M., et al., 1990, "In vivo evidence for protease-catalysed mechanism providing bioactive tumor necrosis factor alpha", Biochemical Pharmacology, vol. 40, pp. 1601-1603.

Novradovsky A, Brantly ML, Waclawiw MA, Chaudhary PP, Ihare H, Qi L, Tony Eissa N. Barnes PM, Gabriele KM, Ehrmantraut ME, Rogliani P, Moss J. Endothelial Nitric Oxide Synthase as a Potential Susceptibility Gene in the Pathogenesis of Emphysema in alphal-Antitrypsin Deficiency. Am J Respir Cell Mol Biol Mar. 1, 1999;20(3):441-447.

Ohnishi et al., "A furin-defective cell line is able to process correctly the gp160 of human immunodeficiency virus type I", J Virol, 68(6):4075-99 (1994).

Okumura et al., "The extracellular processing of HIV-I envelope glycoprotein gp160 by human plasmin", FEBS Lett, 442(1):39-42 (1998).

Ooka T, Hatano Y, Yamamoto M, Ogawa K, Saika S. Protective effects of human urinary trypsin inhibitor against trypsin-induced relaxation in rat aorta. Crit Care Med Nov. 1996;24(11):1903-7.

O'Riordan, K., et al., 1997, "Alpha 1-antitrypsin deficiency-associated panniculitis", Transplantation, vol. 64, pp. 480-482.

Patel R.P., et al. in Biochim Biophys Acta 1999, 1411,385-400.

Patel T, Gores GJ, Kaufmann SH. The role of proteases during apoptosis. FASEB J Apr. 1996;10(5):587-97.

Pellegrini A, Thomas U, Franchini M, Stockli M, Klauser S, Hunziker P, von Fellenberg R. Identification of an aprotinin antiviral domain. FEBS Lett 5-16, 1994;344(2-3):261-5.

Petrache, I., et al., 2006, "alpha-1 Antitrypsin inhibits caspase-3 activity, preventing lung endothelial cell apoptosis", The American Journal of Pathology, vol. 159, No. 4, pp. 1155-1166.

Petrache, I., et al., 2006,"A novel antiapoptotic role for alpha-1 anytrypsin in the prevention of pulmonary emphysema", American Journal of Respiratory Critical Care Medicine, vol. 173, pp. 1222-1228.

Pezzilli R, Gullo L, Ricchi E, Costigliola P, Sprovieri G, Pilati G, Fontana G., "Serum pancreatic enzymes in HIV-seropositive patients", Dig Dis Sci, 37(2):286-8 (Feb. 1992).

Popko B. and Baerwald, K. D. in Neurochem Res 1999, 24, pp. 331-338.

Premack, B. A. and Schell, T. J., "Chemokine Receptors: Gateways to Inflammation and Infection", Nature Medicine, 2, 1174-1178 (1996).

Pryor WA, Dooley MM, Church DF. Mechanisms of cigarette smoke toxicity: the inactivation of human alpha-l-proteinase inhibitor by nitric oxide/isoprene mixtures in air. Chem Biol Interact Jul. 1985;54(2):171-83.

Punjabi, C. J. et al., in J. Immunol. 1992, 149, 2179-2184.

Rehman A, Whiteman M, Halliwell B. Scavenging of hydroxyl radicals but not of peroxynitrite by inhibitors and substrates of nitric oxide synthases. Br J Pharmacol Dec. 1997; 122(8):1702-6.

Remington's Pharmaceutical Sciences 1990, pp. 1519-1675, Gennaro, A. R., ed., Mack Publishing Company, Easton, PA, [Nairn, J. G., Chapter 83].

Rust, C., et al., 2000, "Apoptosis and liver disease", American Journal of Medicine, vol. 108, pp. 567-574.

Scharpe S, De Meester I, Hendriks D, Vanhoof G, van Sande M, Vriend G, "Proteases and their inhibitors: today and tomorrow",-Biochimie, 73(1):121-126 (Jan. 1991).

Schini et al. in Circ Res 1994, 74, 24-32.

Schwartz, et al., "Antiviral activity of the proteasome on incoming human immunodeficiency virus type I", J Virol, 72(5):3845-50) (1998).

Sharpstone D, Rowbottom A, Nelson M, Gazzard B. Faecal alpha I antitrypsin as a marker of gastrointestinal disease in HIV antibody positive individuals. Gut Feb. 1996;38(2):206-10.

Shimizu T, Pommier Y. DNA fragmentation induced by protease activation in p53-null human leukemia HL60 cells undergoing apoptosis following treatment with the topoisomerase I inhibitor camptothecin: cell-free system studies. Exp Cell Res Aug. 1, 1996;226(2):292-301.

Sichko ZhV, Kozlova OL. Experience in treating a herpetic infection with trypsin [Article in Russian]. Vrach Delo Mar. 1991;(3):86-9, English Abstract Only.

Smith, M. E. in Neurochem Res 1999, 24, 261.

Smith, R.M., et al., 1987, "Pulmonary penetration of alpha1-proteinase inhibitor administered parenterally to dogs", American Review of Respiratory Disease, vol. 136, pp. 1391-1396.

Szeghy G, Kenyeres B. On the therapy of herpes simplex keratitis with heparin and trypsin. [Article in German] Klin Monatsbl Augenheilkd 1968;153(6):827-30, English abstract at p. 829.

Tang et al.; "Inactivation of HIV-I by trypsin and its use in demonstrating specific virus infection of cells", J Virol Methods 33(1-2):39-46 (Jun. 1991).

Taraseviciene-Stewart, L., et al., 2008, "Molecular pathogenesis of emphysema", The Journal of Clinical Investigation, vol. 118, pp. 394-402.

Tuder, R. M., et al., 2003, "Apoptosis and emphysema: The missing link", American Journal of Respiratory Cell and Molecular Biology, vol. 28, pp. 551-554.

Turpin JA, Schaeffer CA, Bu M, Graham L, Buckheit RW Jr, Clanton D, Rice WG, "Human immunodeficiency virus type-I (HIV-1) replication is unaffected by human secretory leukocyte protease inhibitor", Antiviral Res, 29(2-3):269-77 (Mar. 1996).

Ueda, N., et al., 2000, "Apoptic mechanisms in acute renal failure", American Journal of Medicine, vol. 108, pp. 403-415.

van Molle et al. Alpha 1-acid glycoprotein and alpha 1-antitrypsin inhibit TNF-induced but not anti-Fas induced apoptosis of hepatocytes in mice. J. Immunol. 1997. 159(7):3555-64.

Van Molle W, Libert C, Fiers W, Brouckaert P. Alpha I-acid glycoprotein and alpha I-antitrypsin inhibit TNF-induced but not anti-Fas-induced apoptosis of hepatocytes in mice. J Immunol Oct. 1, 1997;159(7):3555-64.

Vollenweider F, Benjannet S, Decroly E, Savaria D, Lazure C, Thomas G, Chretien M, Seidah NG, "Comparative cellular processing of the human immunodeficiency virus (HIV-1) envelope glycoprotein gp 160 by the mammalian subtilisin/kexin-like convertases", Biochem, J;314(Pt2):521-32 (Mar. 1996).

Williams, R.S., 1999, "Apoptosis and heart failure", New England Journal of Medicine, vol. 341, pp. 759-760.

Wood, E.R. et al. in Biochem Biophys Res Commun 1993,191, 767-74.

Yamaguchi, Y., et al., 1997, "Neutrophil elastase inhibitor reduces neutrophil chemoattractant production after ischemia-reperfusion in rat liver", Gastroenterology, vol. 122, pp. 551-560.

Zhirnov OP, Ovcharenko AV, Mel'nikova EE, Gaidamovich Sla, Bukrinskaia AG. Antiviral activity of proteinase inhibitors in cultured cells infected with alpha-viruses. Mol Gen Mikrobiol Virusol Dec. 1985;(12):30-6, English abstract at p. 36.

Lieberman, J., Augmentation therapy reduces frequency of lung infections in antitrypsin deficiency: a new hypothesis with supporting data. Chest 2000, 118(5):1480-5.

Panasiuk, A.V. et al., [Disseminated pulmonary tuberculosis, diabetes mellitus and amyloidosis in a patient with hereditary alpha 1-antitrypsin deficiency.] Probl. Tuberk. 1988, 1:72-4.

Daemen, et al., "Functional Protection by Acute Phase Proteins $\alpha_1$-Acid Glycoprotein and $\alpha_1$-Antitrypsin Against Ischemia/Reperfusion Injury by Preventing Apoptosis and Inflammation," Circulation, (Sep. 19, 2000) pp. 1420-1426.

Petrache, et al., "A Novel Antiapoptotic Role for $\alpha_1$-Antitrypsin in the Prevention of Pulmonary Emphysema," Am. J. Respir. and Critical Care Medicine, (2006) vol. 173, pp. 1222-1228.

Taraseviciene-Stewart, et al., "Molecular Pathogenesis of Emphysema," J. Clin. Invest.(2008) 118:394-402 doci: 10.1172/JC131811.

Tuder, et al., "Apoptosis and Emphysema, The Missing Link," Am. J. Respir. Cell Mol. Biol., (2003) 28:551-554.

Bendtzen, et al., "Cytotoxicity of Human $\rho$l 7 Interleukin-1 for Pancreatic Islets of Langerhans," American Association for the Advancement of Science (1986) 232:1545-1547.

Mandrup-Poulsen, et al., "Affinity-purified human Interleukin I is cytotoxic to isolated islets of Langerhans," Diabetologia (1986) 29:63-67.

Mandrup-Poulsen, et al., Human Tumor Necrosis Factor Potentiates Human Interleukin I-Mediated Rat Pancreatic $\beta$-Cell Cytotoxicity, The Journal of Immunology (1987) 139:4077-4082.

Maedler, et al., "Glucose-induced $\beta$ cell production of IL-1$\beta$ contributes to glucotoxicity in human pancreatic islets," The Journal of Immunology (2002) 110:851-860.

Lewis, et al., "$\alpha$1-Antitrypsin monotherapy prolongs islet allograft survival in mice," PNAS (2005), 102:12153-12158.

Strom, "Saving islets from allograft rejection," PNAS (2005) 102:12651-12652.

Emamaullee, et al., "Interventional Strategies to Prevent $\beta$-Cell Apoptosis in Islet Transplantation," Diabetes (2006) 55:1907-1914.

* cited by examiner

METHODS AND COMPOSITIONS FOR TREATING DIABETES

The present application is a continuation of U.S. patent application Ser. No. 09/518,081, filed Mar. 3, 2000, which claims the priority benefit of U.S. Provisional Patent Application No. 60/123,167, filed Mar. 5, 1999, the entire disclosures of which are incorporated by reference herein.

1. FIELD OF THE INVENTION

The present invention relates to compositions and methods useful in the inhibition of apoptosis. Likewise, the present invention relates to methods of treating diseases associated with excessive or unregulated apoptosis.

2. BACKGROUND OF THE INVENTION

Normal development, growth, and function of multi-cellular organisms require control both of processes that produce cells and of those that destroy cells. Mitosis, or cell proliferation, is highly regulated except in specific states termed cell proliferative diseases. There also exist processes for destruction of cells. Cells in multi-cellular organisms die by two distinct mechanisms. One method, termed necrotic cell death, is characterized by cytoplasmic swelling, rupturing of cellular membranes, inflammation and disintegration of subcellular and nuclear components. The other method, apoptosis, by contrast, is characterized by more organized changes in morphology and molecular structure. Apoptotic cells often condense and shrink, in part, by cytoplasmic membrane blebbing, a process of shedding small packets of membrane-bound cytoplasm. The chromosomes of such cells condense around the nuclear periphery. Generally, in apoptotic cells the chromosomes are degraded by specific nucleases that cleave DNA to produce regular-sized fragments. Importantly, there is a requirement for new mRNA and protein expression during the early stages of some forms of apoptosis, indicating that it is an active process. Macrophages envelop and phagocytose apoptotic cells, thereby digesting and recycling the cellular components.

Changes in cell morphology during apoptosis are profound. Detection of the many morphological changes associated with apoptosis is detected using light microscopy or electron microscopy. In particular, electron microscopy is useful for evaluating cells with a high nucleus to cytoplasm ratio and light microscopy is useful for immuno- and histochemistry. The changes characteristic of apoptosis include decreased volume, compaction of cytoplasmic organelles, and increased cell density. In addition, microvilli disappear, blebs of cytoplasm form at the cell surface, and the blebs dissociate from the cell to form apoptotic bodies. Other techniques are useful in the analysis of apoptosis including confocal, laser, and scanning microscopy, fluorescent DNA dye binding, and molecular techniques. The molecular techniques permit detection of apoptosis in formalin-fixed and embedded tissue, including terminal deoxynucleotidyl transferase (TdT)-mediated dUTP-biotin nick end labeling (TUNEL) and in situ, end labeling (ISEL).

Protease Involvement

The progression of apoptosis requires the coordinated action of specific proteases. The proteases can be inhibited by inhibitors including N-tosyl-L-phenylalanylchloromethyl ketone (TPCK) and N-tosyl-L-lysylchloromethyl ketone (TLCK). Furthermore, at least 10 cysteine proteases related to interleukin-1-β converting enzyme have been identified as components of apoptotic signaling pathways. The interleukin-1-β converting enzyme-like proteases are referred to as caspases and are identified and have been isolated by molecular cloning.

In addition, there are other proteases involved in apoptosis including the granzymes and cathepsin. Granzyme B is a serine esterase that can activate several members of the caspase family. Granzyme B may be a mediator of cytotoxic T lymphocyte induced apoptosis. Granzyme B is known to cleave and initiate caspase 3, a likely component of its mode of action. Granzyme B may also initiate nuclear events associated with cytotoxic T lymphocyte-induced apoptosis, consistent with observations that it is passively transported into the nucleus and bind to nuclear proteins. One action of Granzyme B may be in the regulation of conversion of proCPP32 to CPP32. CPP32 is itself a protease thought to cleave poly(ADP-ribose) polymerase (PARP) and may also activate prolamin protease resulting in activation of lamin protease. Cleavage of lamins and inactivation of the DNA repair enzyme PARP promote the development of apoptotic changes in the cell nucleus.

Serine Proteases

In contrast to cysteine proteases, the role of serine proteases in apoptosis is controversial. For a general discussion, see Kaufmann, S. *Cancer Res* 1993, 53, 3976. For example, it is known that the serine protease inhibitor TLCK inhibits apoptosis-associated proteolysis. However, TLCK is known to inhibit cysteine proteases in addition to serine proteases, and has recently been shown to inhibit a member of the interleukin-1β converting enzyme family. Thus, the effect of TLCK on apoptosis is likely not mediated by an effect as a serine protease inhibitor, given the more established role of cysteine proteases in apoptosis.

Cellular Protease Targets

Multiple polypeptide species must be modified to produce the wide range of morphological manifestations that characterize apoptosis. For example, the lamins are nuclear intermediate filament proteins that form a fibrous layer between the inner nuclear membrane and the chromatin. The resulting lamina is thought to play a role in maintaining nuclear shape and in mediating chromatin-nuclear membrane interactions. Thus, the apoptosis-associated changes in nuclear shape might require lamin reorganization. Another polypeptide that is cleaved during apoptosis is poly (ADP-ribose) polymerase (PARP). PARP is an abundant nuclear enzyme that catalyzes the conversion of the dinucleotide $NAD^+$ to nicotinamide and protein-linked chains of ADP-ribose. Yet, the detailed role of PARP in the process of apoptosis is unclear. Studies have suggested that inhibitors of PARP delay apoptosis and yet other studies have suggested that inhibition of PARP increases the fragmentation of DNA during apoptosis. It is clear, however, that PARP is proteolytically degraded late in apoptosis.

Another proteolytic enzyme target during apoptosis is the U1 ribonuclear protein (U1-70k), a molecule required for splicing of precursor mRNA that is itself cleaved to an inactive 40 kDa fragment during apoptosis. The cleavage of this polypeptide would result in cessation of RNA processing.

Other substrates for protease activity during apoptosis include fodrin, the PITSLREβ1 protein kinase, the adenomatous polyposis coli (APC) protein, the retinoblastoma gene product, terminin, and nuclear matrix proteins. Cleavage of fodrin, an abundant membrane associated cytoskeletal protein, has been detected during apoptosis in a variety of cell lines. PITSLREβ1 protein kinase, a member of the $p34^{cdc2}$ gene family has been shown to induce mitotic delay in CHO cells. Members of this family appear to be cleaved during apoptosis. For example, recent studies indicate that PITSL- REβ1 kinase is proteolytically cleaved during FAS- or steroid-induced apoptosis in T-cells. Another major group of protease targets is the caspases, themselves proteases, or precursor forms of caspases. Yet another group of proteins which may well be downstream effectors of caspase-mediated apoptosis, include the protein kinases PKCδ, PKCθ, MEKK1, the sterol regulatory element binding proteins 1 and 2, and the DNA fragmentation factor (DFF).

Diseases Associated with Apoptosis

Increased levels or apparent induction of apoptosis is associated with a number of diseases including cancer, autoimmune diseases including rheumatoid arthritis, neurodegenerative diseases, myocardial infarction, stroke, sepsis, ischemia-reperfusion injury, toxin induced liver injury, and AIDS (see Kidd, V. J., *Annu Rev Physiol*, 1998, 60, 533; List, P. J. M., et al., *Arterioscler Thromb Vasc Biol* 1999, 19, 14; Jabs, T., *Biochem Pharmacol* 1999 57, 231; Deigner, H. P., et al. *Curr Med Chem* 1999, 6, 399). The apoptosis appears to be mediated by oxygen free radicals [O.] which have been implicated in various disorders including atherosclerosis, diabetes, sepsis, Alzheimer's disease, arthritis, muscular dystrophy, cancer, Downs syndrome, multiple sclerosis, HIV infection and other inflammatory diseases (Morel, J. B. and Dangle, J. L., *Cell Death Differ* 1997, 4, 671; Beal, M. F., *Curr Opin Neurobiol* 1996, 6, 661).

3. SUMMARY OF THE INVENTION

The present invention is directed to a method of treating an animal or a patient suffering from a disease characterized by excessive apoptosis. The method of the invention comprises administering a therapeutically effective amount of at least one serine protease inhibitor and subsequently monitoring a decrease in apoptosis.

In a preferred embodiment, the animal is a human. In another preferred embodiment, the agent is $\alpha_1$-antitrypsin (ATT) or an $\alpha_1$-antitrypsin-like agent. In addition, peptides of interest are homologous and analogous peptides. All homologues are natural peptides which have sequence homology, analogs will be peptidyl derivatives, e.g., aldehyde or ketone derivatives of such peptides. Furthermore, agents with $\alpha_1$-antitrypsin-like activity are also envisioned. In this regard, peptide derivatives of $\alpha_1$-antitrypsin, compounds like oxydiazole, thiadiazole, CE-2072, UT-77, and triazole peptoids are preferred. The $\alpha_1$-antitrypsin-like agent includes, but is not limited to, small organic molecules including naturally occurring, synthetic, and biosynthetic molecules, small inorganic molecules including naturally-occurring and synthetic molecules, natural products including those produced by plants and fungi, peptides, variants of $\alpha_1$-antitrypsin, chemically modified peptides, and proteins. It is a further embodiment of this invention that an individual with risk for a pathological disease or condition that is precipitated at least in part by excessive apoptosis, can be treated to prevent the onset of acute disease with a prophylactic treatment of an agent exhibiting $\alpha_1$-antitrypsin or $\alpha_1$-antitrypsin-like activity.

A further embodiment of the invention envisions a method for inhibiting apoptosis in an in vitro mammalian cell culture, an ex vivo mammalian tissue culture, or a mammalian organ, comprising providing to a cell culture, tissue culture, or organ, an amount of a serine protease inhibitor sufficient to inhibit apoptosis in the cell culture, tissue culture, or organ. In the aforementioned embodiment, a measured amount of apoptosis is indicative of expression or activity of apoptosis.

A still further embodiment of the invention directed to a method of inhibiting apoptosis comprises allowing a serine protease inhibitor to bind to a protease and measuring the decrease in apoptosis. Another embodiment of the invention is directed to a method of inhibiting apoptosis comprising allowing a serine protease inhibitor to bind to a cell surface receptor and measuring the decrease in apoptosis.

A yet still further embodiment of the invention is directed to use of oxidation-resistant and free-radical resistant inhibitors of serine proteases. In this regard, the oxidation-sensitive $Met^{358}$ in $\alpha_1$-antitrypsin can, by genetic engineering, be replaced by $Val^{358}$-$\alpha_1$-antitrypsin, which results in a molecule termed $Val^{358}$-$\alpha_1$-antitrypsin. $Val^{358}$-$\alpha_1$-antitrypsin is a more potent inhibitor of neutrophil elastase than is $Met^{358}$-$\alpha_1$-antitrypsin possibly because of the stability of $Val^{358}$-$\alpha_1$-antitrypsin to the neutrophil oxidative burst. The Met at position 358 is replaced with any hydrophobic or neutral oxidation-resistant amino acid residue, including: alanine, asparagine, α-amino butyric acid, anthranilic acid, β-cyanoalanine, β-(3,4-dihyroxyphenyl) alanine, 3,5-diiodotyrosine, glutamine, glycine, homoserine, 3-hydroxyanthranilic acid, 5-hydroxy-indole-3-acetic acid, 3-hydroxykynurenine, hydroxyproline, 5-hydroxy-tryptophan, indoleacetic acid, 3-iodotyrosine, isoleucine, alloisoleucine, leucine, leucylglycine, norleucine, norvaline, phenylalanine, proline, prolylglycine, serine, threonine, allothreonine, throxine, 3,5,3'-tri-iodo-thyronine, tryptophan, and tyrosine. The amino acid substitutions are effected by genetic engineering, chemical modification, or a combination thereof.

5. DETAILED DESCRIPTION OF THE INVENTION

5.1 Standard Methods

In accordance with the present invention there can be employed conventional molecular biology, microbiology, and recombinant DNA techniques within the skill of the art. Such techniques are explained fully in the literature. See, e.g., Sambrook, Fritsch & Maniatis, *Molecular Cloning. A Laboratory Manual, Second Edition* 1989, Cold Spring Harbor Laboratory Press, Cold Spring Harbor, N.Y.; *Animal Cell Culture, R. I. Freshney, ed.,* 1986).

5.2 Serine Protease Inhibitors

The current invention teaches methodologies and agents for treating animals and patients that suffer from a disease involving excessive apoptosis. The methods involve administration of therapeutically effective amounts of at least one serine protease inhibitor and testing for changes in apoptosis by any of several means known in the art. The serine proteases that are inhibited by the agent of the invention include trypsin, elastase, cathepsin G, tryptase TL-2, Factor Xa and proteinase-3. The methods further involve inhibition of oxygen free radicals and inhibition of oxygen free radical formation by serine protease inhibitors. The method further includes a pharmaceutically acceptable carrier, any of which are known in the art. Serine protease inhibitors include $\alpha_1$-antitrypsin, or $\alpha_1$-antitrypsin-like agents. In the latter group are included the oxydiazole, thiazole, triazole peptoids, or some combination of these agents. The serine protease inhibitor is optionally derivatized chemically by esterification, acetylation or amidation.

There are numerous diseases that are characterized by excessive apoptosis. Among these diseases are cancer, autoimmune diseases, neurodegenerative diseases, myocardial infarction, stroke, ischemia-reperfusion injury, toxin-induced liver injury, sepsis and AIDS.

A preferred embodiment of the invention is directed toward the treatment of myocardial infarction. Another preferred embodiment of the invention is directed toward treatment of stroke, also known as brain ischemia or cerebrovascular accident. The therapeutically effective amounts of the serine protease inhibitors are sufficient to bring the concentration of the added agent in the biological fluid of the individual to between about 10 pM and 2 mM. For $\alpha_1$-antitrypsin the effective concentrations correspond to between about 5 nanograms per milliliter to about 10 milligrams per milliliter of the biological fluid of the individual. The biological fluid of the individual is calculated from the total body weight of the individual or, in diseases that are localized to specific body compartments, from the volume of the compartment. Biological fluid can include, but is not limited to, blood, plasma, serum, lymph, tears, saliva, cerebrospinal fluid, or combinations thereof.

In a preferred embodiment of the invention, the therapeutically effective amount is sufficient to bring the concentration in the biological fluid to between 0.5 µM and 200 µM, preferably between 5 µM and 200 µM, most preferably about 100 µM. The agent is advantageously administered according to the weight of the subject. Administration of the therapeutically effective amount of serine protease inhibitor can be in a bolus, for example, of about 0.001 to 7 g of $\alpha_1$-antitrypsin-like agent or about 1 to 70 g of $\alpha_1$-antitrypsin, per kg of body weight of the subject. Preferred amounts are about 0.01 g/kg body weight of oxydiazole, thiazole, or triazole peptoids, and about 1 g/kg body weight of natural or variant $\alpha_1$-antitrypsin.

The administration of the agent in the invention can be performed parenterally, orally, vaginally, nasally, buccally, intravenously, intramuscularly, subcutaneously, rectally, intrathecally, epidurally, transdermally, intracerebroventricularly, or combinations thereof.

In another embodiment of the invention, the agent is administered continuously or intermittently by osmotic pump or by implanted osmotic pump, including those of the Alza Corporation. It is a further embodiment of the invention that the therapeutically effective amount of the serine protease inhibitor is administered between about once daily to about once hourly. In a more preferred embodiment of the invention, the serine protease inhibitor is administered twice per day. It is a further embodiment of the invention that the monitoring of changes in apoptosis be performed on tissue obtained from an animal or patient. Any of several methods for monitoring apoptosis, well known in the art, are suitable.

A further method of the invention is directed to encouraging the binding of a serine protease inhibitor to a protease and observing a change in apoptosis. In this embodiment, the serine protease inhibitor is $\alpha_1$-antitrypsin or $\alpha_1$-antitrypsin-like agent. The $\alpha_1$-antitrypsin-like agent is also a substituted oxydiazole, substituted thiadiazole, substituted triazole peptoids, or any combination of these agents.

Apoptosis is associated with free radical production, including oxygen free radicals. Free radicals are known to inactivate natural $\alpha_1$-antitrypsin. Therefore, it is desirable to supplement $\alpha_1$-antitrypsin in blood with sufficient $\alpha_1$-antitrypsin-like activity which is not inactivated by free radicals. Alternatively, a mutant $\alpha_1$-antitrypsin resistant to inactivation by free radicals, or administration of a synthetic molecule that is not inactivated by free radicals, is contemplated. Also, co-administration of a free radical scavenger or inhibitor is contemplated.

The present invention is not limited by the mechanism of action of $\alpha_1$-antitrypsin inhibitors in decreasing apoptosis. Thus the apoptosis may be mediated by tumor necrosis factor, by anti-Fas or by any other mechanism. In a particular embodiment of the invention apoptosis not mediated by tumor necrosis factor is inhibited by the $\alpha_1$-antitrypsin-like agents of the invention. Moreover, the agents of the invention are effective to inhibit apoptosis in a plurality of organs including, but not limited to brain, heart, spinal cord, peripheral nerves, skin, stomach, liver, pancreas, gut, ovaries, testis, and endocrine glands.

It is to be understood that the present invention is not limited to the examples described herein, and other serine protease inhibitors known in the art are used within the limitations of the invention. For example, one skilled in the art can easily adopt inhibitors as described in WO 98/24806, which discloses substituted oxadiazole, thiadiazole and triazole as serine protease inhibitors. U.S. Pat. No. 5,874,585 discloses substituted heterocyclic compounds useful as inhibitors of serine proteases including: (benzyloxycarbonyl)-L-valyl-N-[1-(3-(5-(3-trifluoromethylbenzyl)-1,2,4-oxadiazolyl)carbonyl)-2-(S)-methylpropyl]-L-prolinamide benzyloxycarbonyl)-L-valyl-N-[1-(3-(5-(2-phenylethyl)-1,2,4-oxadiazolyl)carbonyl)-2-(S)-methylpropyl]-L-prolinamide; (benzyloxycarbonyl)-L-valyl-N-[1-(3-(5-(2-methoxybenzyl)-1,2,4-oxadiazolyl)carbonyl)-2-(S)-methylpropyl]-L-prolinamide; (benzyloxycarbonyl)-L-valyl-N-[1-(3-(5-(trifluoromethyl)-1,2,4-oxadiazolyl)carbonyl)-2-(S)-methylpropyl]-L-prolinamide; (benzyloxycarbonyl)-L-valyl-N-[1-(3-(5-(methyl)-1,2,4-oxadiazolyl)carbonyl)-2-(S)-Methylpropyl]-L-Prolinamide; (Benzyloxycarbonyl)-L-Valyl-N-[1-(3-(5-(difluoromethyl)-1,2,4-oxadiazolyl)carbonyl)-2-(S)-Methylpropyl]-L-Prolinamide; (Benzyloxycarbonyl)-L-Valyl-N-[1-(3-(5-(benzyl)-1,2,4-oxadiazolyl)carbonyl)-2-(S)-Methylpropyl]-L-Prolinamide; (Benzyloxycarbonyl)-L-Valyl-N-[1-(3-(5-(3-methoxybenzyl)-1,2,4-oxadiazolyl)carbonyl)-2-(S)-Methylpropyl]-L-Prolinamide; (Benzyloxycarbonyl)-L-Valyl-N-[1-(3-(5-(2,6-difluorobenzyl)-1,2,4-oxadiazolyl)carbonyl)-2-(S)-Methylpropyl]-L-Prolinamide; (Benzyloxycarbonyl)-L-Valyl-N-[1-(3-(5-(trans-styryl)-1,2,4-oxadiazolyl)carbonyl)-2-(S)-Methylpropyl]-L-Prolinamide; (Benzyloxycarbonyl)-L-Valyl-N-[1-(3-(5-(trans-4-Trifluoromethylstyryl)-1,2,4-oxadiazolyl)carbonyl)-2-(S)-Methylpropyl]-L-Prolinamide; (Benzyloxycarbonyl)-L-Valyl-N-[1-(3-(5-(trans-4-Methoxystyryl)-1,2,4-oxadiazolyl)carbonyl)-2-(S)-Methylpropyl]-L-Prolinamide; (Benzyloxycarbonyl)-L-Valyl-N-[1-(3-(5-(3-Thienylmethyl)-1,2,4-oxadiazolyl)carbonyl)-2-(S)-Methylpropyl]-L-Prolinamide; (Benzyloxycarbonyl)-L-Valyl-N-[1-(3-(5-(Phenyl)-1,2,4-oxadiazolyl)carbonyl)-2-(S)-Methylpropyl]-L-prolinamide; and (Benzyloxycarbonyl)-L-Valyl-N-[1-(3-(5-(3-Phenylpropyl)-1,2,4-oxadiazolyl)carbonyl)-2-(S)-Methylpropyl]-L-Prolinamide. U.S. Pat. No. 5,216,022 teaches other small molecules useful for the practice of this invention, including: Benzyloxycarbonyl-L-valyl-N-[1-(2-[5-(3-methylbenzyl)-1,3,4-oxadiazolyl]carbonyl)-2-(S)-methylpropyl]-L-prolinamide (also known as CE-2072), Benzyloxycarbonyl-L-valyl-N-[1-(2-(3-methylbenzyl)-1,3,4-oxadiazolyl]carbonyl)-2-(S)-methylpropyl]-L-prol inamide; Benzyloxycarbonyl-L-valyl-N-[1-(2-(5-(methyl)-1,3,4-oxadiazolyl]carbonyl)-2-(S)-methylpropyl]-L-prolinamide; Benzyloxycarbonyl)-L-valyl-N-[1-(2-(5-(3-trifluoromethylbenzyl)-1,3,4-oxadiazolyl]carbonyl)-2-(S)-methylpropyl]-L-prolinamide;

(Benzyloxycarbonyl)-L-valyl-N-[1-(2-(5-(4-Dimethylamino benzyl)-1,3,4-oxadiazolyl]carbonyl)-2-(S)-methylpropyl]-L-prolinamide; Benzyloxycarbonyl)-L-valyl-N-[1-(2-(5-(1-napthylenyl)-1,3,4-oxadiazolyl]carbonyl)-2-(S)-methylpropyl]-L-prolinamide; (Benzyloxycarbonyl)-L-valyl-[1-(3-(5-(3,4-methylenedioxybenzyl)-1,2,4-oxadiazolyl]carbonyl)-2-(S)-methylpropyl]-L-prolinamide; Benzyloxycarbonyl)-L-valyl-N-[1-(3-(5-(3,5-dimethylbenzyl)-1,2,4-oxadiazolyl]carbonyl)-2-(S)-methylpropyl]-L-prolinamide; (Benzyloxycarbonyl)-L-valyl-N-[1-(3-(5-(3,5-dimethoxybenzyl)-1,2,4-oxadiazolyl]carbonyl)-2-(S)-methylpropyl]-L-prolinamide; (Benzyloxycarbonyl)-L-valyl-N-[1-(3-(5-(3,5-ditrifluoromethylbenzyl)-1,2,4-oxadiazolyl]carbonyl)-2-(S)-methylpropyl]-L-prolinamide; (Benzyloxycarbonyl)-L-valyl-N-[1-(3-(5-(3-methylbenzyl)-1,2,4-oxadiazolyl]carbonyl)-2-(S)-methylpropyl]-L-prolinamide; (Benzyloxycarbonyl)-L-valyl-N-[1-(3-(5-(biphenylmethine)-1,2,4-oxadiazolyl]carbonyl)-2-(S)-methylpropyl]-L-prolinamide; (Benzyloxycarbonyl)-L-valyl-N-[1-(3-(5-(4-phenylbenzyl)-1,2,4-oxadiazolyl]carbonyl)-2-(S)-methylpropyl]-L-prolinamide; (Benzyloxycarbonyl)-L-valyl-N-[1-(3-(5-(3-phenylbenzyl)-1,2,4-oxadiazolyl]carbonyl)-2-(S)-methylpropyl]-L-prolinamide; (Benzyloxycarbonyl)-L-valyl-N-[1-(3-(5-(3-phenoxybenzyl)-1,2,4-oxadiazolyl]carbonyl)-2-(S)-methylpropyl]-L-prolinamide; (Benzyloxycarbonyl)-L-valyl-N-[1-(3-(5-(cyclohexylmethylene)-1,2,4-oxadiazolyl]carbonyl)-2-(S)-methylpropyl]-L-prolinamide; (Benzyloxycarbonyl)-L-valyl-N-[1-(3-(5-(3-trifluoromethyldimethylmethylene)-1,2,4-oxadiazolyl]carbonyl)-2-(S)-methylpropyl]-L-prolinamide; (Benzyloxycarbonyl)-L-valyl-N-[1-(3-(5-(1-napthylmethylene)-1,2,4-oxadiazolyl]carbonyl)-2-(S)-methylpropyl]-L-prolinamide; (Benzyloxycarbonyl)-L-valyl-N-[1-(3-(5-(3-pyridylmethyl)-1,2,4-oxadiazolyl]carbonyl)-2-(S)-methylpropyl]-L-prolinamide; (Benzyloxycarbonyl)-L-valyl-N-[1-(3-(5-(3,5-diphenylbenzyl)-1,2,4-oxadiazolyl]carbonyl)-2-(S)-methylpropyl]-L-prolinamide; (Benzyloxycarbonyl)-L-valyl-N-[1-(3-(5-(4-dimethylaminobenzyl)-1,2,4-oxadiazolyl]carbonyl)-2-(S)-methylpropyl]-L-prolinamide; 2-(5-[(Benzyloxycarbonyl)amino]-6-oxo-2-(4-fluorophenyl)-1,6-dihydro-1-pyrimidinyl]-N-[1-(3-(5-(3-trifluoromethylbenzyl)-1,2,4-oxadiazolyl]carbonyl)-(S)-2-methylpropyl]acetamide; 2-(5-Amino-6-oxo-2-(4-fluorophenyl)-1,6-dihydro-1-pyrimidinyl]-N-[1-(3-(5-(3-trifluoromethylbenzyl)-1,2,4-oxadiazolyl]carbonyl)-2-(S)-methylpropyl]acetamide; 2-(5-[(Benzyloxycarbonyl)amino]-6-oxo-2-(4-fluorophenyl)-1,6-dihydro-1-pyrimidinyl]-N-[1-(2-(5-(3-methylbenzyl)-1,3,4-oxadiazolyl]carbonyl)-(S)-2-methylpropyl]acetamide; 2-(5-Amino-6-oxo-2-(4-fluorophenyl)-1,6-dihydro-1-pyrimidinyl]-N-[1-(2-(5-(3-methylbenzyl)-1,3,4-oxadiazolyl]carbonyl)-2-methylpropyl]acetamide; (Pyrrole-2-carbonyl)-N-(benzyl)glycyl-N-[1-(2-(5-(3-methylbenzyl)-1,3,4-oxadiazolyl]carbonyl)-2-(S)-methylpropyl]amide; (Pyrrole-2-carbonyl)-N-(benzyl)glycyl-N-[1-(3-(5-(3-trifluoromethylbenzyl)]-1,2,4-oxadiazolyl)-(S)-methylpropyl]amide; (2S,5S)-5-Amino-1,2,4,5,6,7-hexahydroazepino-[3,2,1]-indole-4-one-carbonyl-N-[1-(2-(5-(3-methylbenzyl)-1,3,4-oxadiazolyl]carbonyl)-(R,S)-2-methylpropyl]amide; BTD-[1-(2-(5-(3-methylbenzyl)-1,3,4-oxadiazolyl]carbonyl)-2-(S)-methylpropyl]amide; (R,S)-3-Amino-2-oxo-5-phenyl-1,4,-benzodiazepine-N-[1-(2-(5-(3-methylbenzy 1)-1,3,4-oxadiazolyl]carbonyl)-2-(S)-methylpropyl]acetamide; (Benzyloxycarbonyl)-L-valyl-2-L-(2,3-dihydro-1-indole)-N-[1-(2-(5-(3-methylbenzyl)-1,3,4-oxadiazolyl]carbonyl)-2-(S)-methylpropyl]amide; (Benzyloxycarbonyl)-L-valyl-2-L-(2,3-dihydro-1H-indole)-N-[1-(3-(5-(3-trifluoromethylbenzyl)-1,2,4-oxadiazolyl]carbonyl)-2-(S)-methylpropyl]amide; Acetyl-2-L-(2,3-dihydro-1H-indole)-N-[1-(2-(5-(3-methylbenzyl)-1,3,4-oxadiazolyl]carbonyl)-2-(S)-methylpropyl]amide; 3-(S)-(Benzyloxycarbonyl)amino)-F-lactam-N-[1-(2-(5-(3-methylbenzy 1)-1,3,4-oxadiazolyl]carbonyl)-2-(S)-methylpropyl]acetamide; 3-(S)-(Amino)-S-lactam-N-[1-(2-(5-(3-methylbenzyl)-1,3,4-oxadiazolyl]carbonyl)-2-(S)-methylpropyl]acetamide trifluoroacetic acid salt; 3-(S)-[(4-morpholino carbonyl-butanoyl)amino]-ϵ-lactam-N-[1-(2-(5-(3-methylbenzyl)-1,3,4-oxadiazolyl]carbonyl)-2-(R,S)-methylpropyl]acetamide; 6-[4-Fluorophenyl]-ϵ-lactam-N-[1-(2-(5-(3-methylbenzyl)-1,3,4-oxadiazolyl]carbonyl)-2-(S)-methylpropyl]acetamide; 2-(2-(R,S)-Phenyl-4-oxothiazolidin-3-yl]-N-[1-(2-(5-(3-methylbenzyl)-1,3,4-oxadiazolyl]carbonyl)-2-(S)-methylpropyl]acetamide; 2-(2-(R,S)-phenyl-4-oxothiazolidin-3-yl]-N-[1-(2-(5-(3-methylbenzyl)-1,3,4-oxadiazolyl] hydroxymethyl)-2-(S)-methylpropyl]acetamide; 2-(2-(R,S)-Benzyl-4-oxothiazolidin-3-yl]-N-[1-(2-(5-(3-methylbenzyl)-1,3,4-oxadiazolyl]carbonyl)-2-(S)-methylpropyl]-acetamide; 2-(2-(R,S)-Benzyl-4-oxothiazolidin-3-yl oxide]-N-[1-(3-(5-(3-trifluoromethylbenzyl)-1,2,4-oxadiazolyl]carbonyl)-2-(R, S,)-methylpropyl]acetamide; (1-Benzoyl-3,8-quinazolinedione)-N-[1-(2-(5-(3-methylbenzyl)-1,3,4-oxadiazolyl]carbonyl)-2-(S)-methylpropyl]acetamide; (1-Benzoyl-3,6-piperazinedione)-N-[1-(2-(5-(3-methylbenzyl)-1,3,4-oxadiazolyl]carbonyl)-2-(S)-methylpropyl]acetamide; (1-Phenyl-3,6-piperazinedione)-N-[1-(2-(5-(3-methylbenzyl)-1,3,4-oxadiazolyl]carbonyl)-2-(S)-methylpropyl] acetamide; [(1-Phenyl-3,6-piperazinedione)-N-[1-(3-(5-(3-trifluoromethylbenzyl)-1,2,4-oxadiazolyl]carbonyl)]-2-(S)-methylpropyl]acetamide; 3-[(Benzyloxycarbonyl)amino]-quinolin-2-one-N-[1-(2-(5-(3-methylbenzyl)-1,3,4-oxadiazolyl]carbonyl)-2-(S)-methylpropyl]acetamide; 3-[(Benzyloxycarbonyl)amino]-7-piperidinyl-quinolin-2-one-N-[1-(2-(5-(3-methylbenzyl)-1,3,4-oxadiazolyl]carbonyl)-2-(S)-methylpropyl]acetamide; 3-(Carbomethoxy-quinolin-2-one-N-[1-(2-(5-(3-methybenzyl)-1,3,4-oxadiazoly]carbonyl)-2-(S)-methylpropyl]acetamide; 3-(Amino-quinolin-2-one)-N-[1-(2-(5-(3-methylbenzyl)-1,3,4-oxadiazolyl]carbonyl)-2-(S)-methylpropyl]acetamide; 3-[(4-Morpholino)aceto]amino-quinolin-2-one-N-[1-(2-(5-(3-methylbenzyl)-1, 3,4-oxadiazolyl]carbonyl)-2-(S)-methylpropyl]acetamide; 3,4-Dihydro-quinolin-2-one-N-[1-(2-(5-(3-methylbenzyl)-1,3,4-oxadiazolyl]carbonyl)-2-(S)-methylpropyl]acetamide; 1-Acetyl-3-(4-fluorobenzylidene)piperazine-2,5-dione-N-[1-(2-(5-(3-methylbenzyl)-1,3,4-oxadiazolyl]carbonyl)-2-(S)-methylpropyl]acetamide; 1-Acetyl-3-(4-dimethylamino benzylidene)piperazine-2,5-dione-N-[1-(2-(5-(3-methylbenzyl)-1,3,4-oxadiazolyl]carbonyl)-2-(S)-methylpropyl]acetamide; 1-Acetyl-3-(4-carbomethoxy benzylidene)piperazine-2,5-dione-N-[1-(2-(5-(3-methylbenzyl)-1,3,4-oxadiazolylcarbonyl)-2-(S)-methylpropyl acetamide; 1-Acetyl-3-[(4-pyridyl)methylene] piperazine-2,5-dione-N-[1-(2-(5-(3-methyl benzyl)-1,3,4-oxadiazolyl]carbonyl)-2-(S)-methylpropyl]acetamide; 4-[1-Benzyl-3-(R)-benzyl-piperazine-2,5-dione]-N-[1-(2-[5-(3-methylbenzyl)-1,3,4-oxadiazolyl]carbonyl)-2-(S)-methylpropyl]acetamide; 4-[1-Benzyl-3-(S)-benzyl piperazine-2,5-dione]-N-[1-(2-(5-(3-methylbenzyl)-1,3,4-oxadiazolyl]carbonyl)-2-(S)-methylpropyl]acetamide; 4-[1-Benzyl-3(R)-benzylpiperazine-2,5-dione]-N-[1-(3-(5-(3-trifluoromethylbenzyl)-1,2,4-oxadiazolyl]carbonyl)-2-(S)-methylpropyl]acetamide; 4-[1-Benzyl-3-(S)- benzylpiperazine-2,5,-dione]-N-[1-(3-(5-(3-trifluoromethylbenzyl)-1,2,4-oxadiazolyl]carbonyl)-2-(S)-methylpropyl]acetamide; 4-[1-Benzyl-3-(S)-benzyl piperazine-2,5,-dione]-N-[1-(3-(5-(2-dimethylaminoethyl)-1,2,4-oxadiazolyl]carbonyl)-2-(S)-methylpropyl]acetamide; 4-[1-Methyl-3-(R,S)-phenylpiperazine-2,5,-dione]-N-[1-(3-(5-(3-trifluoromethylbenzyl)-1,2,4-oxadiazolyl]carbonyl)-2-(S)-methylpropyl]acetamide; 4-[1-Methyl-3-(R,S)-phenyl piperazine-2,5,-dione]-N-[1-(2-(5-(3-methylbenzyl)-1,3,4-oxadiazolyl]carbonyl)-2-(S)-methylpropyl]acetamide; 4-[1-(4-Morpholino ethyl)3-(R)-benzyl piperazine-2,5,-dione]-N-[1-(2-(5-(3-methylbenzyl)-1,3,4-oxadiazolyl]carbonyl)-2-(S)-methylpropyl]acetamide; 5-(R,S)-Phenyl-2,4-imidazolidinedione-N-[1-(2-(5-(3-methylbenzyl)-1,3,4-oxadiazolyl]carbonyl)-2-(S)-methylpropyl]acetamide; 5-(R)-Benzyl-2,4-imidazolidinedione-N-[1-(2-(5-(3-methylbenzyl)-1,3,4-oxadiazolyl]carbonyl)-2-(S)-methylpropyl] acetamide; 5-(S)-Benzyl-2,4-imidazolidinedione-N-[1-(2-(5-(3-methylbenzyl)-1,3,4-oxadiazolyl]carbonyl)-2-(S)-methylpropyl]acetamide; 5-(S)-Benzyl-2,4-imidazolidinedione-N-[1-(3-(5-(3-trifluoromethylbenzyl)-1,2,4-oxadiazolyl]carbonyl)-2-(S)-methylpropyl]acetamide; 5-(R)-Benzyl-2,4-imidazolidinedione-N-[1-(3-(5-(3-trifluoromethylbenzyl)-1,2,4-oxadiazolyl]carbonyl)-2-(S)-methylpropyl]acetamide; 1-Benzyl-4-(R)-benzyl-2,5-imidazolidinedione-N-[1-(2-(5-(3-methylbenzyl)-1,3,4-oxadiazolyl]carbonyl)-2-(S)-methylpropyl]acetamide; and 1-Benzyl-4-(R)-benzyl-2,5-imidazolidinedione-N-[1-(3-(5-(3-trifluoromethyl benzyl)-1,2,4-oxadiazolyl]carbonyl)-2-(S)-methylpropyl]acetamide among others.

Yet another embodiment of the invention is directed toward the inhibition of apoptosis resulting from the interaction between a serine protease inhibitor and a cell surface receptor and resulting in a measurable decrease in apoptosis. The serine protease inhibitor of this embodiment is an $\alpha_1$-antitrypsin or an $\alpha_1$-antitrypsin-like agent. The $\alpha_1$-antitrypsin-like agents includes substituted oxydiazoles, substituted thiadiazole, substituted triazole peptoids, or combinations of these agents. The substituted oxydiazole, thiadiazole, and triazole peptoids are synthesized de novo or derivatized from existing compounds.

5.3. Diseases Addressed by the Invention

Specific diseases or disorders for which the therapeutic methods of the invention are beneficial include wasting diseases of various types. The diseases include cancer, neurodegenerative diseases, myocardial infarction, and stroke. The cancers include bladder, breast, kidney, leukemia, lung, myoloma, liposarcoma, lymphoma, tongue, prostate, and uterine cancers. The method of the invention is also applied to Alzheimer's disease, arthritis, muscular dystrophy, Downs Syndrome, sepsis, HIV infection, multiple sclerosis, arteriosclerosis, diabetes, and arthritis. In fact, the invention is applied to any disease associated with elevated levels of apoptosis.

5.4. Modes of Administration

Modes of administration of the various therapeutic agents used in the invention are exemplified in the examples below. However, the agents are delivered by any of a variety of routes including: by injection (e.g., subcutaneous, intramuscular, intravenous, intra-arterial, and intraperitoneal), by continuous intravenous infusion, transdermally, orally (e.g., tablet, pill, liquid medicine), by implanted osmotic pumps (e.g., ALZA Corp.), by suppository or aerosol spray.

Those skilled in the art of biochemical synthesis will recognize that for commercial scale quantities of peptides, such peptides are preferably prepared using recombinant DNA techniques, synthetic techniques, or chemical derivatization of biologically or chemically synthesized peptides.

The compounds of the present invention are used as therapeutic agents in the treatment of a physiological, or especially, pathological, condition caused in whole or part by uncontrolled serine protease and apoptosis activity. The peptides or peptoids can be administered as free peptides, free peptoids, or pharmaceutically acceptable salts thereof. The terms used herein conform to those in Budavari, S. (Ed.), "The Merck Index, An Encyclopedia of Chemicals, Drugs, and Biologicals," Merck Company, Inc., twelfth edition. The term "pharmaceutically acceptable salt" refers to those acid addition salts or methyl complexes of the peptides which do not significantly or adversely affect the therapeutic properties including efficacy and toxicity, of the peptides and peptoids. The peptides and peptoids are administered to individuals as a pharmaceutical composition which, in most cases, will comprise the peptide, peptoid, and/or pharmaceutical salts thereof with a pharmaceutically acceptable carrier. The term "pharmaceutically acceptable carrier" refers to those solid and liquid carriers, which do not significantly or adversely affect the therapeutic properties of the peptides.

The pharmaceutical compositions containing peptides and/or peptoids of the present invention are administered to individuals, particularly humans, either intravenously, subcutaneously, intramuscularly, intranasally, orally, topically, transdermally, parenterally, gastrointestinally, transbronchially, and transalveolarly. Topical administration is accomplished by a topically applied cream, gel, rinse, etc. containing therapeutically effective amounts of inhibitors of serine proteases. Transdermal administration is accomplished by administration of a cream, rinse, gel, etc. capable of allowing the inhibitors of serine proteases to penetrate the skin and enter the blood stream. Parenteral routes of administration include, but are not limited to, direct injection such as intravenous, intramuscular, intraperitoneal, or subcutaneous injection. Gastrointestinal routes of administration include, but are not limited to, ingestion and rectal. Transbroncheal and transalveolar routes of administration include, but are not limited to, inhalation, either via the mouth or intranasally, and direct injection into an area, such as through a tracheotomy, endotracheal tube, or aspirated through a respiratory mist. In addition, osmotic pumps are used for administration. The necessary dosage will vary with the particular condition being treated, method of administration, and rate of clearance of the molecule from the body.

6. EXAMPLES

The following specific examples are provided to better assist the reader in the various aspects of practicing the present invention. As these specific examples are merely illustrative, nothing in the following descriptions should be construed as limiting the invention in any way. Such limitations are, of course, defined solely by the accompanying claims.

6.1. Effect of therapy with $\alpha_1$-antitrypsin following Experimental Myocardial Infarction or Stroke Rats (female, 250-300 g each) are randomly assigned to one of four groups: myocardial infarction control, stroke control, myocardial infarction, and stroke. The rats are subjected to a 30 minute ligation of the coronary arterial supply (for the myocardial infarction group) or the left carotid artery (for the stroke group), followed by release of the ligature. Sham operated controls receive the cut-down and manipulation of the artery but without ligation. Immediately preceding the ligation or sham ligation, half of the animals in each group (by random selection) receive $\alpha_1$-antitrypsin (sufficient to achieve a 50 µM concentration of added agent in the blood, or in the alternative, an amount equal to 10 mg/kg body weight) and the other half receive a body-weight equivalent volume of AAT vehicle, intravenously. The AAT vehicle is phosphate-buffered saline, or optionally, any pharmaceutically acceptable carrier. At twenty-four hours after release of the sham or actual ligation the animals are sacrificed and the hearts and brains removed for analysis of the amount of apoptosis. In other experiments the dosage of $\alpha_1$-antitrypsin administered is varied between the amounts necessary to produce a concentration of 10 µM and 250 µM in the blood. In general, a concentration of 5 mg/ml of $\alpha_1$-antitrypsin is equivalent to about 100 µM. In yet other experiments the frequency of administration is varied from once per day to four times per day. Likewise, antielastase and antiproteinase are used.

6.2. Anti-Apoptosis Therapy for Septic Shock

Protection of mouse L929 cells from apoptotic effects of TNF are evaluated using: the agents $\alpha_1$-antitrypsin; (Benzyloxycarbonyl)-L-Valyl-N-[1-2-3(5-(3-methylbenzyl)-1,3,4-oxadiazolyl)carbonyl)-2-(S)-Methylpropyl]-L-Prolinamide; (Benzyloxycarbonyl)-L-Valyl-N-[1-(3-(5-(2-Phenylethyl)-1,2,4-oxadiazolyl)carbonyl)-2-(S)-Methylpropyl]-L-Prolinamide; and (Benzyloxycarbonyl)-L-Valyl-N-[1-(3-(5-(2-Methoxybenzyl)-1,2,4-oxadiazolyl)carbonyl)-2-(S)-Methylpropyl]-L-Prolinamide L929. Cells ($10^5$ cells/well) are treated with 300 ng/ml of human Tumor Necrosis Factor (TNF) with or without the agent (added one hour prior to TNF addition) at 0.02, 0.1, 0.2, 1.0, 2.0 and 10 mg agent/ml. One day later the cells are stained for viability using 2'-[4-hydroxyphenyl]-5-[4-methyl-1-piperazinyl]-2,5'-bi-1H-benzimidazole and fluorescence analyzed for apoptosis using a Leitz fluorescence microscope. The results are evaluated in terms of the dose response to the agent.

6.3. Free Radical Scavengers as Co-Inhibitors of Apoptosis

Agents that reduce free radical levels do not directly prevent the oxidizing effect of free radicals. Therefore, it is advantageous to administer two or three independently acting agents, as opposed to a single agent. Thus, one preferred embodiment of the process is the co-administration of $\alpha_1$-antitrypsin and a free radical scavenger, such as glutathione (1 mg/kg body weight).

6.4. Free Radical Scavengers as Co-Inhibitors of Apoptosis

In yet another embodiment of the invention, oxidation-resistant (xI-antitrypsin variants are used to avoid inactivation by excess free radicals. As an example, synthetic $\alpha_1$-antitrypsin or recombinant $\alpha_1$-antitrypsin produced with alternative and oxidation-resistant amino acid sequences are embodiments of the invention.

6.5. Effect of AAT and CE-2072 on Apoptosis in RCG Neuron Cells

Figure 1:
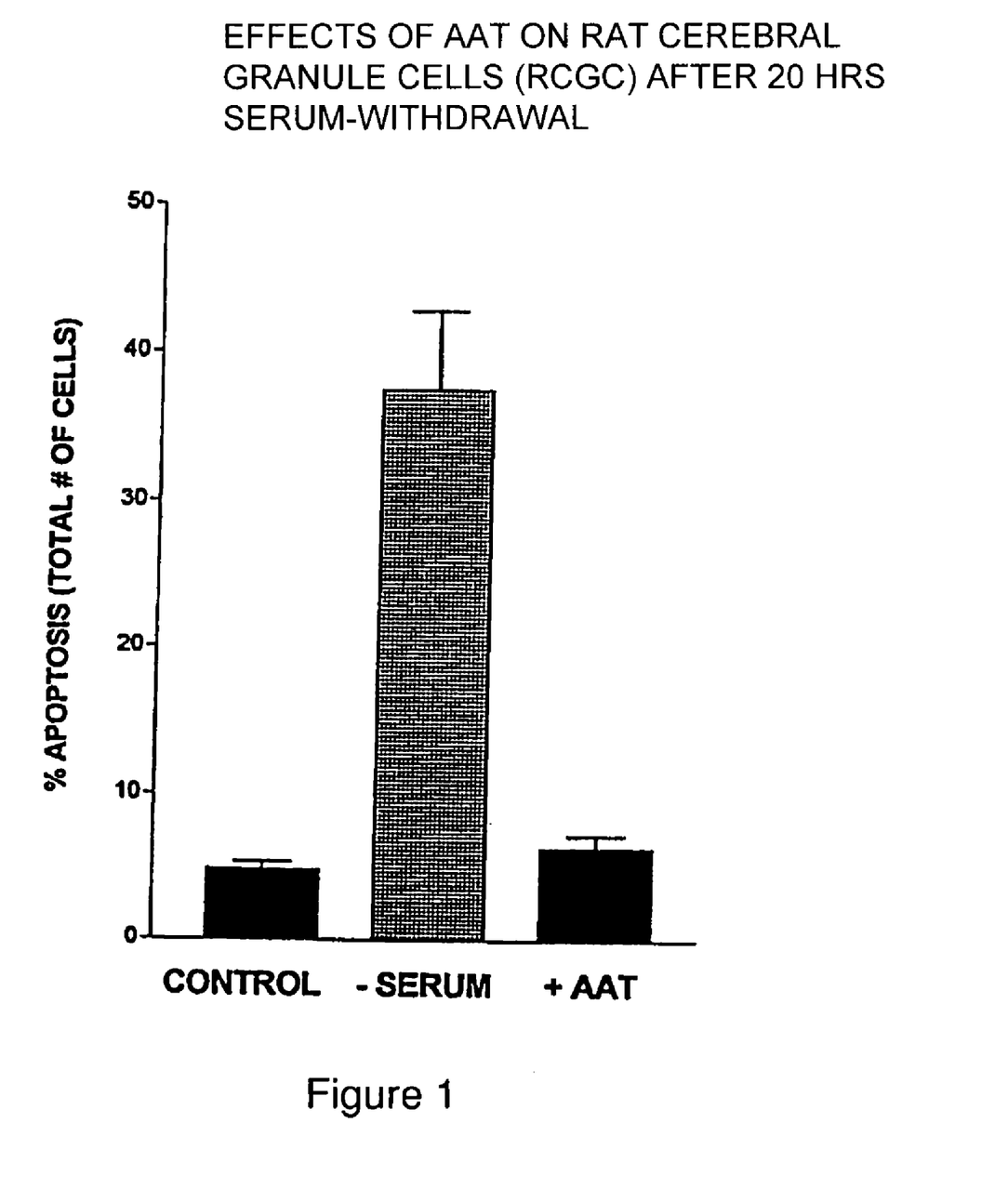
FIG. 1 illustrates the effect of $\alpha_1$-antitrypsin on apoptosis in primary rat brain cerebral granule cells.
Figure 2:
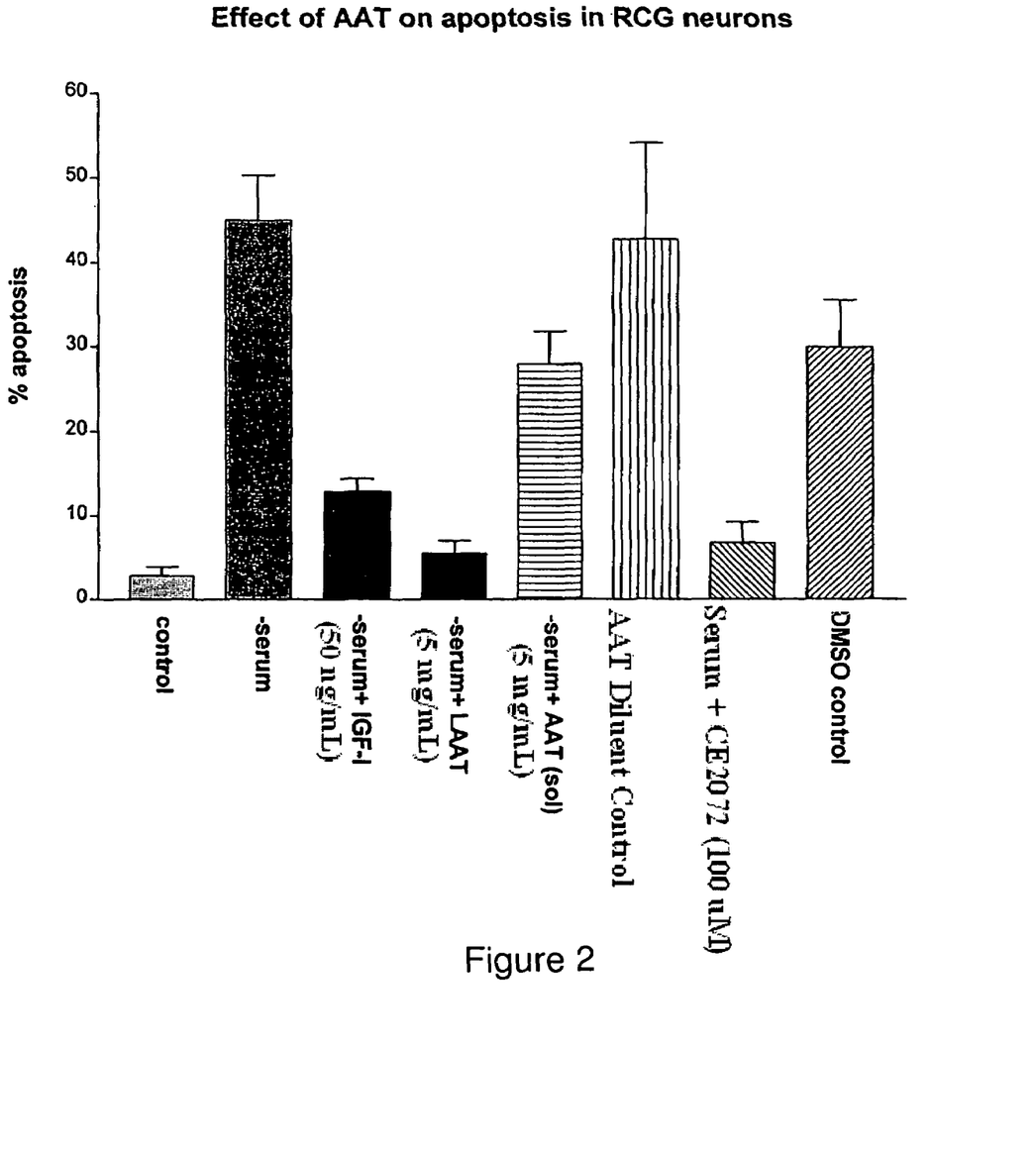
FIG. 2 illustrates the effect of $\alpha_1$-antitrypsin and the peptoid CE-2072 on apoptosis in RCG Neuron (rat cerebral granule) cells, also termed RCGC.

RCG neuronal cells are seeded into cell culture dishes in 400 µl cell culture medium (Eagle's basal medium, BME) containing 10% (v/v) FBS. At day two the now conditioned medium is removed and the cells are treated for 10 hours as follows:

| Group | Condition | Treatment |
| --- | --- | --- |
| 1. | negative control | conditioned medium with serum |
| 2. | positive control | BME without serum |
| 3. | experimental | BME without serum, with IGF-I (50 ng/ml) |
| 4. | experimental | BME without serum, with lyophilized AAT (50 µM) |
| 5. | experimental | BME without serum, with soluble AAT (50 µM) |
| 6. | experimental | BME without serum, with CE-2072 (60 µM) in DMSO |
| 7. | diluent control | BME without serum, with vehicle |
| 8. | DMSO control | BME without serum, with DMSO |

Then the medium is replaced with 4% (w/v) paraformaldehyde, incubated for 15 minutes at room temperature, and the cells stained with Hoechst dye 33258 (8 µg/ml) for 15 minutes at room temperature. The apoptosis in the cells is evaluated using a fluorescence microscope by an evaluator blinded to the method of treatment. The results are shown in FIG. 2.

The apoptosis induced by depletion of serum is blocked by lyophilized $\alpha_1$-antitrypsin and by agent CE-2072 (a synthetic inhibitor of serine protease). The latter is formally known as benzyloxycarbonyl-L-valyl-N-[1-(2-[5-(3-methylbenzyl)-1,3,4-oxadiazolyl]carbonyl)-2-(S)-Methylpropyl]-L-prolinamide.

6.6. Amelioration of Ischemia in Donor Organs During Transport and Transplant

Human donor organs, including kidneys, are subject to ischemia during transport, which can last up to several hours. Biopsies (3 mm) are removed from the top medial surface of donor kidneys undergoing transport prior to implantation, and grouped by time after removal from the donor: 1-2 hours, 2-4 hours, and greater than 4 hours. Donor kidneys transplanted within one hour serve as the first control and the contralateral kidney serves as the second control. Half of the donor kidneys are treated with $\alpha_1$-antitrypsin (10 mg/ml fluid) upon removal from the donor to inhibit apoptosis.

6.7. Therapy with Oxidation-Resistant Recombinant $\alpha_1$-Antitrypsin Variants Val$^{358}$-antitrypsin and Ile$^{358}$-antitrypsin are produced from the appropriate nucleotide sequences by methods well known in the art, including construction of a plasmid, transfection of the host *E. coli*, selection of transfected colonies, expansion of the culture, and isolation and purification of the mutant gene product. Amounts of the recombinant agents effective in inhibiting apoptosis, excessive clotting, neutrophil extravasation, ischemia-reperfusion injury, or myocardial damage are applied in an experimental model of myocardial infarction (see Example 6.1, supra). Effective amounts are between 0.03 and 7 g/kg body weight, for example, about 0.5 g/kg. In some experiments the amount of variant antitrypsin is measured in the blood or other biological fluid. In those tests sufficient variant antitrypsin is administered to provide a concentration of about 1 µM to about 100 µM in the blood or biological fluid.

6.8. Effect of $\alpha_1$-Antitrypsin on Apoptosis

Primary rat brain granule cells are pretreated for one hour in the absence or presence of $\alpha_1$-antitrypsin (3.0 mg/ml), followed by replacement of the cell culture medium with either control medium containing 10% (vol/vol) fetal bovine serum, medium devoid of fetal bovine serum, or medium devoid of fetal bovine serum but containing $\alpha_1$-antitrypsin. After 24 hours of culture the level of apoptosis is measured. $\alpha_1$-Antitrypsin completely reverses the apoptosis associated with serum depletion, which results in cell death.

Throughout this application various publications and patents are referenced. The disclosures of these publications and patents in their entireties are hereby incorporated by reference into this application in order to more fully describe the state of the art to which this invention pertains. While the invention has been described in connection with specific embodiments thereof, it will be understood that it is capable of further modifications, and this application is intended to cover any variations, uses, or adaptations of the invention following, in general, the principles of the invention and including such departures from the present disclosure has come within known or customary practice within the art to which the invention pertains and as can be applied to the essential features here before set forth and as follows in the scope of the appended claims.

The invention claimed is:

1. A method for treating diabetes in a subject in need thereof, said method consisting of administering a therapeutically effective amount of alpha-1-antitrypsin (AAT) polypeptide to treat diabetes in the subject.

2. The method of claim 1, wherein the AAT is substantially purified from a mammalian source or is a recombinantly-produced AAT.

3. The method of claim 2, wherein the recombinantly-produced AAT is isolated from a culture of transformed cells.

4. The method of claim 1, wherein the amount of AAT or the oxidation-resistant or free-radical resistant derivative thereof administered to the subject ranges from about 0.1 g/kg to about 1g/kg of body weight of the subject.

5. The method of claim 1, wherein the AAT is administered nasally, parenterally, orally, buccally, intravenously, intramuscularly, subcutaneously, intrathecally, transdermally, by inhalation, by osmotic pump, or a combination thereof.

6. The method of claim 1, wherein the subject is a human.

7. The method of claim 1, wherein the AAT is administered at least once daily.

* * * * *